(12) United States Patent
Hyde et al.

(10) Patent No.: US 9,075,906 B2
(45) Date of Patent: Jul. 7, 2015

(54) MEDICAL SUPPORT SYSTEM INCLUDING MEDICAL EQUIPMENT CASE

(71) Applicant: Elwha LLC, Bellevue, WA (US)

(72) Inventors: Roderick A. Hyde, Redmond, WA (US); Jordin T. Kare, Seattle, WA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 89 days.

(21) Appl. No.: 13/930,928

(22) Filed: Jun. 28, 2013

(65) Prior Publication Data

US 2015/0002606 A1 Jan. 1, 2015

(51) Int. Cl.
*H04N 7/14* (2006.01)
*G06F 19/00* (2011.01)

(52) U.S. Cl.
CPC ............ *G06F 19/3418* (2013.01); *H04N 7/142* (2013.01); *G06F 19/327* (2013.01)

(58) Field of Classification Search
CPC ..... G06F 19/3418; H04N 7/142; H04N 7/147
USPC .................. 128/200.14; 206/438, 534; 221/2; 312/36; 368/10; 604/67; 700/237; 705/3; 726/17; 200/43.01; 307/62; 340/540, 542; 348/14.02; 439/34
See application file for complete search history.

(56) References Cited

U.S. PATENT DOCUMENTS

| | | | | |
|---|---|---|---|---|
| 4,843,373 A | * | 6/1989 | Trickle et al. .................. | 340/540 |
| 5,014,875 A | * | 5/1991 | McLaughlin et al. ............ | 221/2 |
| 5,164,707 A | * | 11/1992 | Rasmussen et al. .......... | 340/551 |
| 5,694,919 A | * | 12/1997 | Rubsamen et al. ...... | 128/200.14 |
| 6,056,716 A | | 5/2000 | D'Antonio et al. | |
| 6,169,707 B1 | * | 1/2001 | Newland .......................... | 368/10 |
| 6,398,727 B1 | | 6/2002 | Bui et al. | |
| 6,579,242 B2 | | 6/2003 | Bui et al. | |
| 6,830,549 B2 | | 12/2004 | Bui et al. | |
| 6,925,357 B2 | | 8/2005 | Wang et al. | |
| 7,044,744 B2 | * | 5/2006 | Sellien ............................. | 439/34 |
| 7,142,945 B2 | | 11/2006 | Wang et al. | |

(Continued)

FOREIGN PATENT DOCUMENTS

DE 10240904 A1 3/2004

OTHER PUBLICATIONS

U.S. Appl. No. 14/089,478, Hyde et al.

(Continued)

*Primary Examiner* — Gerald Gauthier
(74) *Attorney, Agent, or Firm* — Advent, LLP

(57) ABSTRACT

A medical equipment case is provided for containing and transporting at least one article of medical equipment and a two-way audio-visual system. Such equipment may be used, for example, for telemedicine applications by a patient discharged from a hospital, or other subject in need of remote health care monitoring. The medical equipment case may include features that provide for security and facilitate return of the medical equipment case and medical equipment and audio-visual system contained therein, such as machine-readable indicia encoding information for return of the case from a usage location. The medical equipment case and contained medical equipment and two-way audio visual system together form a medical support system that can be used by a patient discharged from a hospital. Methods of controlling the medical support system are also described.

32 Claims, 13 Drawing Sheets

(56) References Cited

U.S. PATENT DOCUMENTS

| | | | |
|---|---|---|---|
| 7,142,947 B2 | 11/2006 | Wang et al. | |
| 7,158,860 B2 | 1/2007 | Wang et al. | |
| 7,161,322 B2 | 1/2007 | Wang et al. | |
| 7,164,969 B2 | 1/2007 | Wang et al. | |
| 7,164,970 B2 | 1/2007 | Wang et al. | |
| 7,171,286 B2 | 1/2007 | Wang et al. | |
| 7,218,992 B2 | 5/2007 | Wang et al. | |
| 7,249,036 B2 | 7/2007 | Bayne | |
| 7,289,211 B1 | 10/2007 | Walsh, Jr. et al. | |
| 7,894,651 B2 | 2/2011 | Gutkowicz-Krusin et al. | |
| 8,074,273 B2 * | 12/2011 | Oowaki et al. | 726/17 |
| 8,117,046 B2 | 2/2012 | Bayne | |
| 8,121,673 B2 | 2/2012 | Tran | |
| 8,125,549 B2 | 2/2012 | Dekel | |
| 8,199,244 B2 | 6/2012 | Baraniuk et al. | |
| 8,208,698 B2 | 6/2012 | Bogdan | |
| D669,587 S | 10/2012 | Mayer | |
| 8,348,885 B2 | 1/2013 | Moberg et al. | |
| 8,452,446 B1 | 5/2013 | Madris et al. | |
| 8,544,645 B2 | 10/2013 | Edwards et al. | |
| 8,544,646 B2 * | 10/2013 | Bouhraoua et al. | 206/438 |
| 8,648,269 B2 * | 2/2014 | Steele et al. | 200/43.01 |
| 2002/0138017 A1 | 9/2002 | Bui et al. | |
| 2003/0130590 A1 | 7/2003 | Bui et al. | |
| 2005/0060198 A1 | 3/2005 | Bayne | |
| 2005/0256392 A1 | 11/2005 | Matory et al. | |
| 2007/0055166 A1 | 3/2007 | Patil | |
| 2007/0112464 A1 | 5/2007 | Wang et al. | |
| 2008/0004907 A1 | 1/2008 | Bayne | |
| 2008/0275315 A1 | 11/2008 | Oka et al. | |
| 2008/0309487 A1 * | 12/2008 | Chao | 340/542 |
| 2009/0043253 A1 * | 2/2009 | Podaima | 604/67 |
| 2009/0093688 A1 | 4/2009 | Mathur | |
| 2009/0154781 A1 | 6/2009 | Bogdan | |
| 2009/0182582 A1 * | 7/2009 | Hammon | 705/3 |
| 2009/0227877 A1 | 9/2009 | Tran | |
| 2009/0236954 A1 * | 9/2009 | Kobayashi et al. | 312/36 |
| 2009/0276090 A1 * | 11/2009 | Rajiv | 700/237 |
| 2009/0292552 A1 | 11/2009 | Chen et al. | |
| 2009/0301925 A1 * | 12/2009 | Alloro et al. | 206/534 |
| 2009/0306487 A1 | 12/2009 | Crowe et al. | |
| 2011/0064287 A1 | 3/2011 | Bogdan | |
| 2011/0105853 A1 | 5/2011 | Rakowski et al. | |
| 2011/0144455 A1 | 6/2011 | Young et al. | |
| 2012/0041275 A1 | 2/2012 | Sota et al. | |
| 2012/0095352 A1 | 4/2012 | Tran | |
| 2012/0095357 A1 | 4/2012 | Tran | |
| 2012/0101371 A1 | 4/2012 | Verdooner | |
| 2012/0157800 A1 | 6/2012 | Tschen | |
| 2012/0197439 A1 | 8/2012 | Wang et al. | |
| 2012/0197464 A1 | 8/2012 | Wang et al. | |
| 2012/0224753 A1 | 9/2012 | Bogdan | |
| 2012/0268462 A1 | 10/2012 | Sota et al. | |
| 2012/0307056 A1 | 12/2012 | Zuzak et al. | |
| 2013/0083185 A1 | 4/2013 | Coleman, III | |
| 2013/0128223 A1 | 5/2013 | Wood et al. | |
| 2013/0278067 A1 * | 10/2013 | Poss et al. | 307/62 |
| 2015/0002606 A1 * | 1/2015 | Hyde et al. | 348/14.02 |

OTHER PUBLICATIONS

U.S. Appl. No. 14/089,446, Hyde et al.

U.S. Appl. No. 14/068,188, Hyde et al.

Feng et al., "Computer-assisted technique for the design and manufacture of realistic facial prostheses", British Journal of Oral and Maxillofacial Surgery, Accepted May 2010, pp. 105-109, vol. 48, Elsevier Ltd.

Majid et al., "Integration of stereophotogrammetry and triangulation-based laser scanning system for precise mapping of craniofacial morphology", The International Archives of the Photogrammetry, Remote Sensing and Spatial Information Sciences, 2008, pp. 805-811, vol. XXXVII, Part B5.

Markiewicz et al., "The Use of 3D Imaging Tools in Facial Plastic Surgery"; Facial Plast Surg Clin N Am, 2011, pp. 655-682, vol. 19, Elsevier Inc.

Shi et al., "Non-contact Reflection Photoplethysmography Towards Effective Human Physiological Monitoring", Journal of Medical and Biological Engineering, 2010, pp. 161-167, vol. 30, No. 3.

Van Heerbeek et al., "Three dimensional measurement of rhinoplasty results", Rhinology, 2009, pp. 121-125, vol. 47.

"Cisco TelePresence VX Clinical Assistant™" Installation and User Guide, Jun. 2012, pp. 1-33, Cisco Systems, Inc.

"FacileCare for Home", SoftPro Telemedicine and Healthcare, printed on May 23, 2013, pp. 1-2, http://www.softpro.it/telemedicine/home-care.aspx, SoftPro.

Lamonica, Martin, "iRobot Puts Telemedicine on Auto Pilot", MIT Technology Review, Jul. 26, 2012, pp. 1-4, http://www.technologyreview.com/view/428623/irobot-puts-telemedicine-on-auto-pilot/, MIT Technology Review.

"Making Remote Presence Routine", InTouch Health, printed on May 23, 2013, pp. 1-2, http://www.intouchhealth.com/products-and-services/products/, InTouch Technologies, Inc.

Meier, Scott, "White Paper Connecting Patients and Physicians Reducing Health Care Costs", HealthNetConnect, Apr. 2012, pp. 1-17, Health Net Connect, Inc.

"RP-Xpress", InTouch Health, printed on May 23, 2013, pp. 1-1, http://www.intouchhealth.com/products-and-services/products/rp-xpress/, InTouch Technologies, Inc.

"Transitional Care", InTouch Health, printed on May 23, 2013, pp. 1-1, http://www.intouchhealth.com/clinical-uses/transitional-care/, InTouch Technologies, Inc.

* cited by examiner

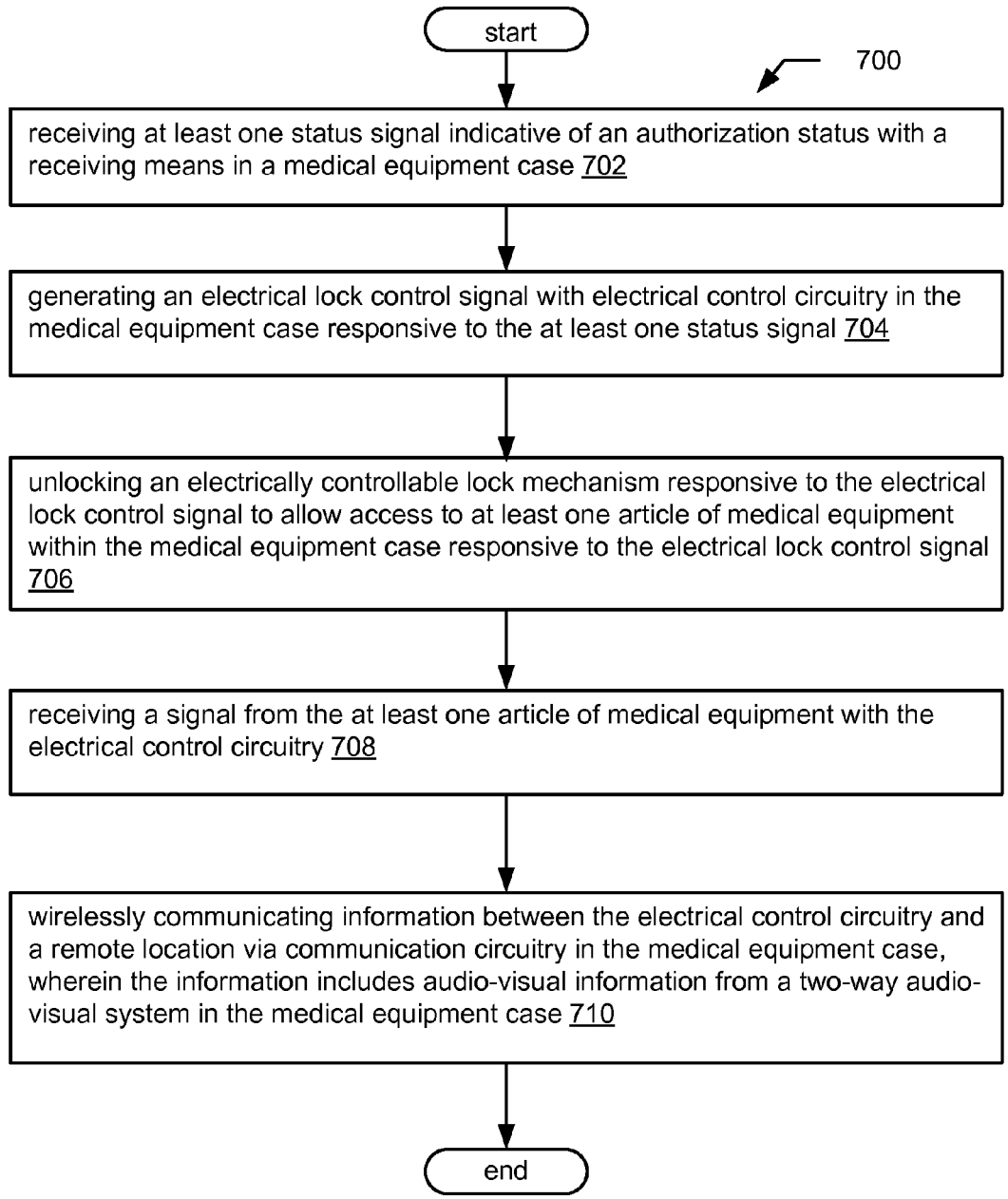

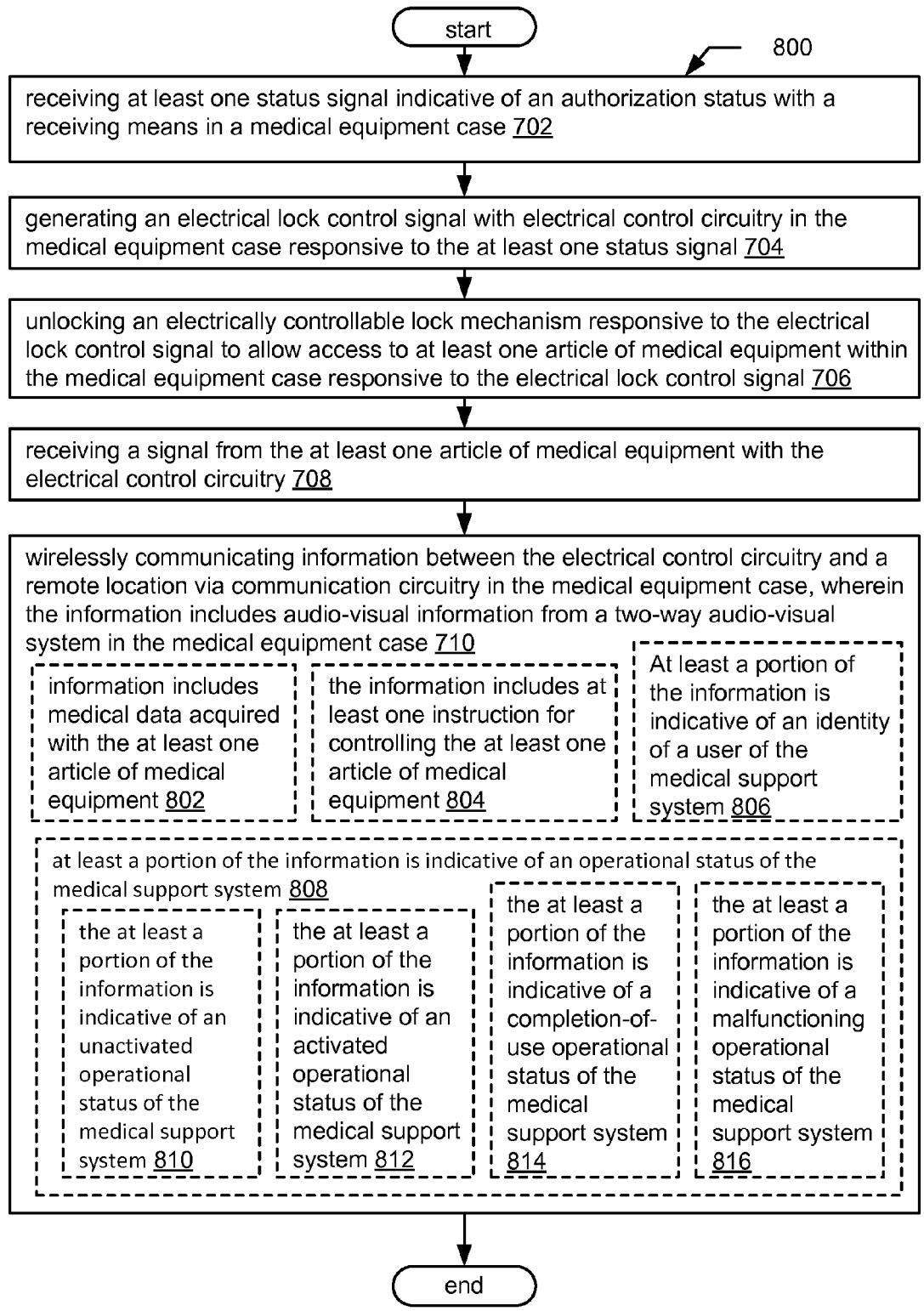

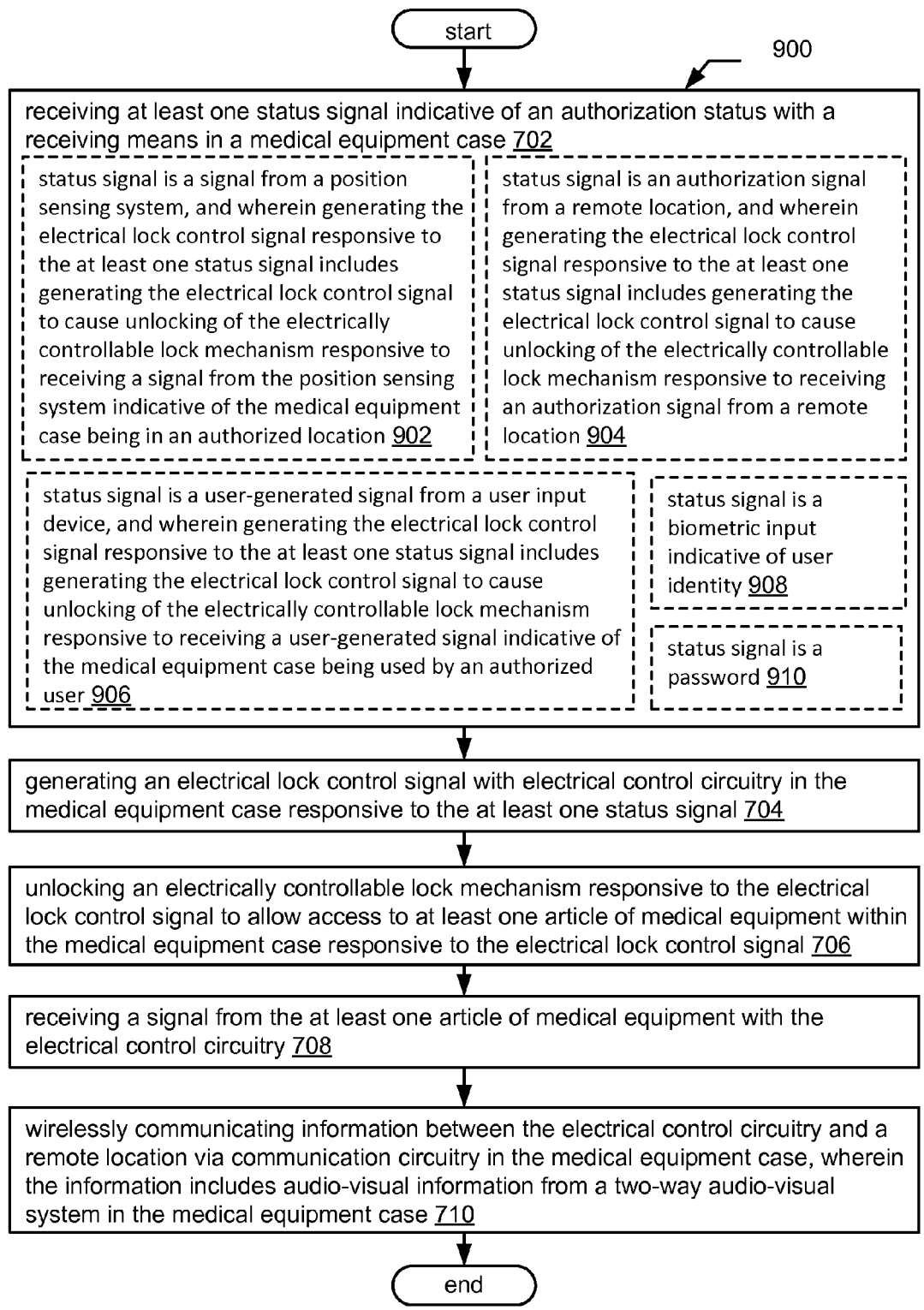

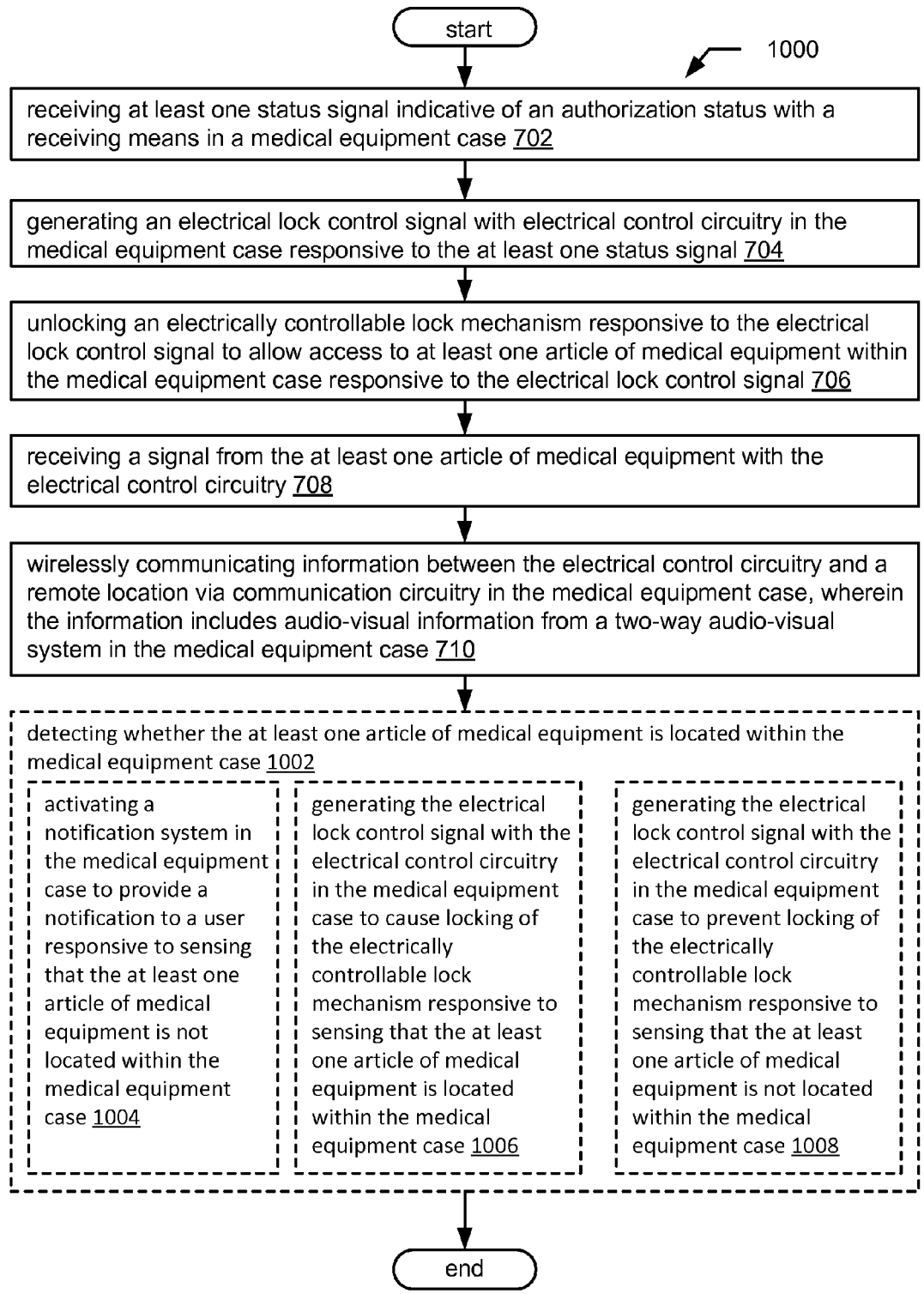

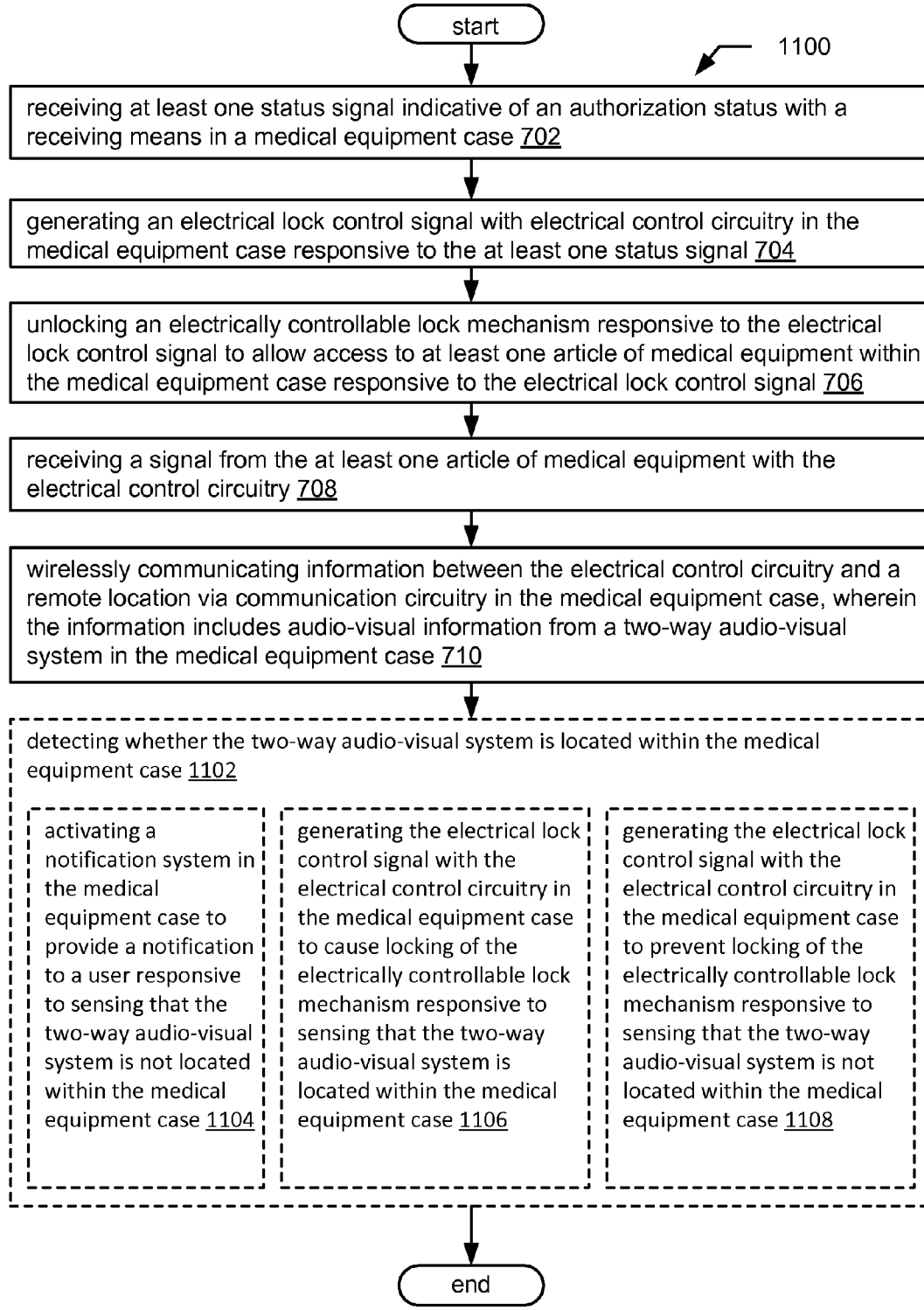

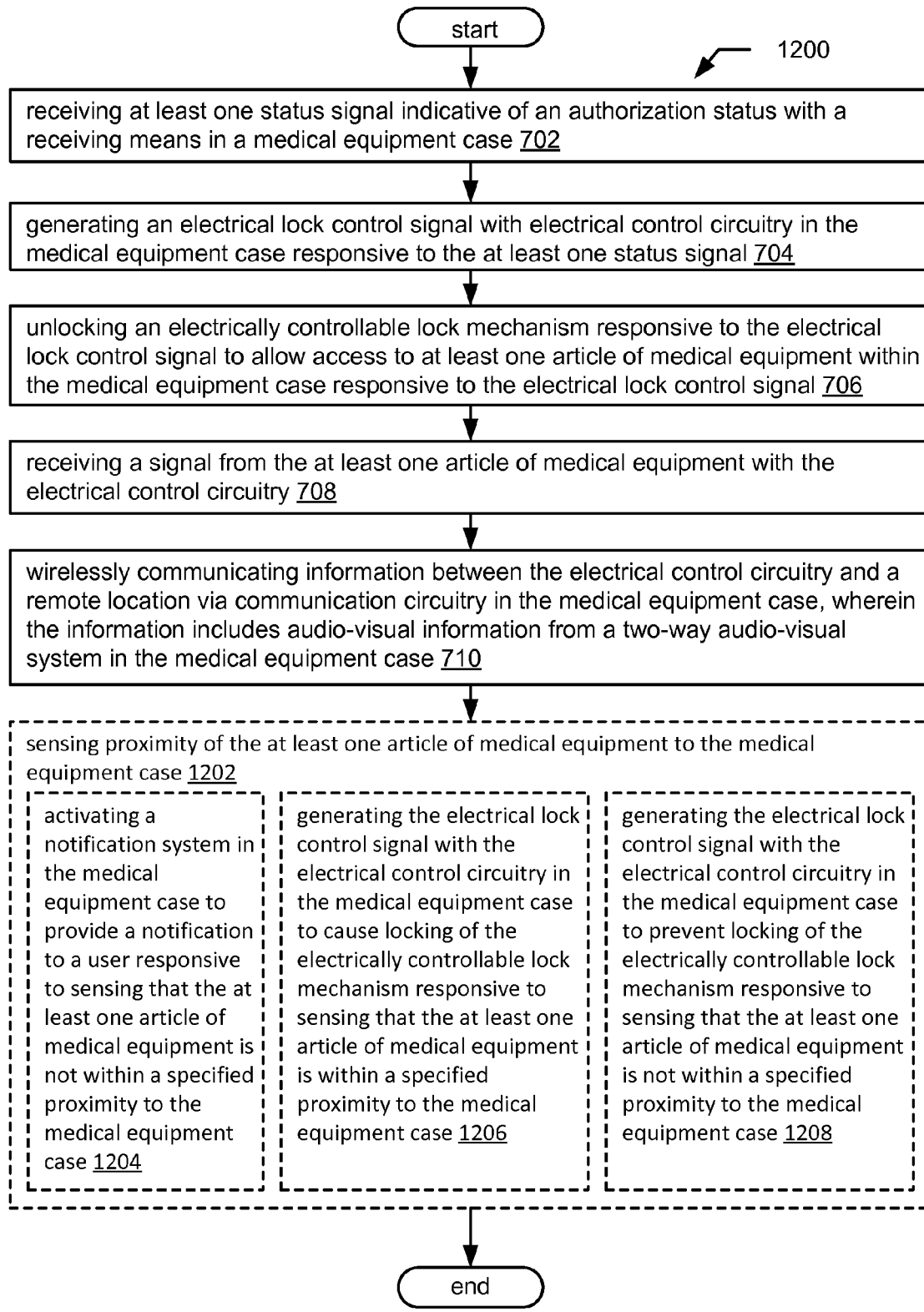

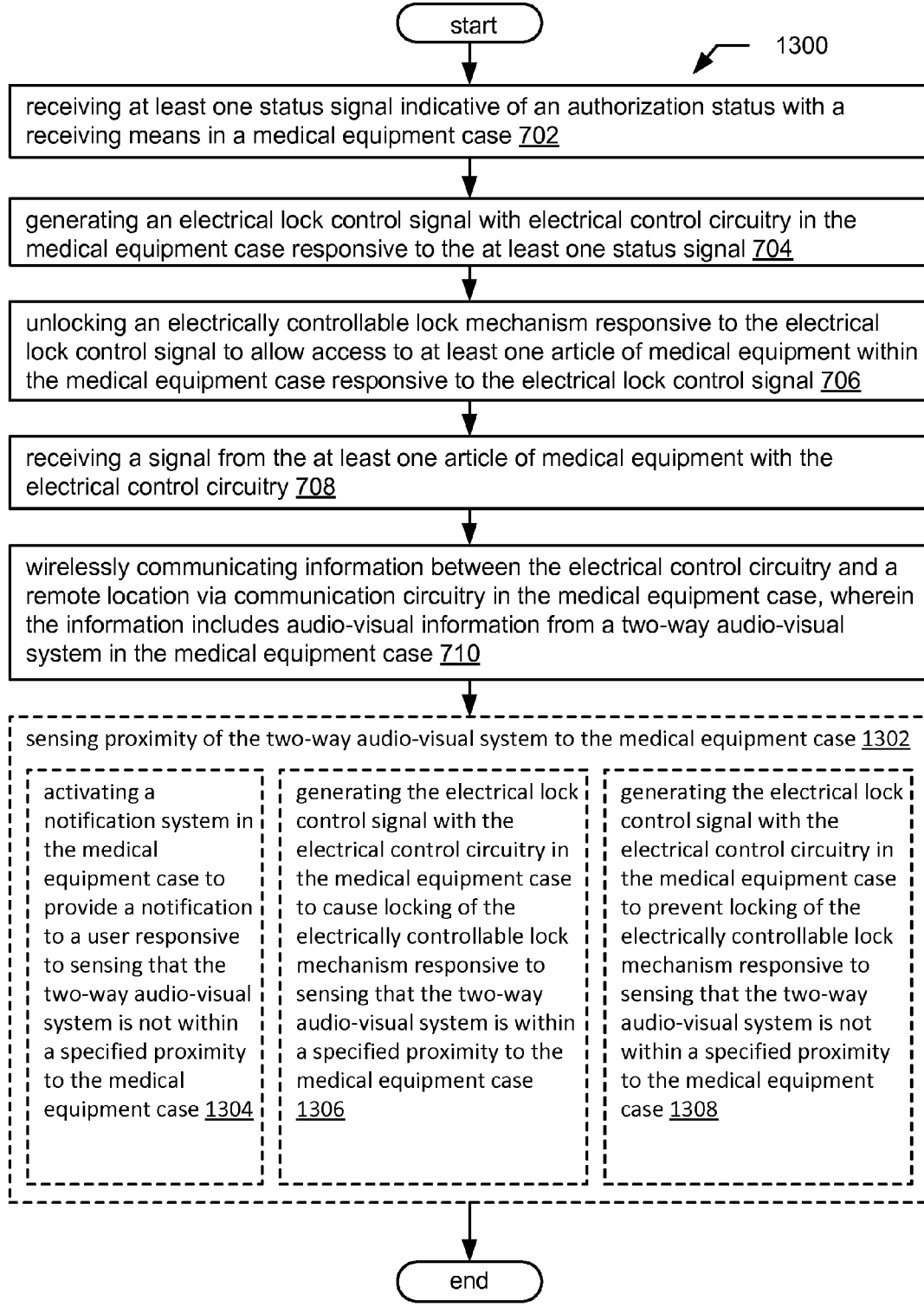

MEDICAL SUPPORT SYSTEM INCLUDING MEDICAL EQUIPMENT CASE

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None.

RELATED APPLICATIONS

None.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, a medical equipment case includes a shell sized and configured for transport by a human; a first receptacle within the shell sized and shaped to receive at least one article of medical equipment; a second receptacle within the shell sized and shaped to receive a two-way audio-visual system; at least one cover adapted to allow access to the at least one article of medical equipment received within the first receptacle when in an open configuration and to enclose and protect the at least one article of medical equipment received within the first receptacle when in a closed configuration; electrical control circuitry located within the shell and configured for communication with the at least one article of medical equipment and the two-way audio-visual system; communication circuitry for providing wireless communication between the electrical control circuitry and a remote location; and machine-readable indicia accessible from outside the case when the cover is in a closed configuration, the machine-readable indicia encoding information for return of the case from a usage location to a return location. In addition to the foregoing, other system aspects are described in the claims, drawings, and text forming a part of the disclosure set forth herein.

In an aspect, a medical support system includes a medical equipment case including a shell sized and configured for transport by a human; a first receptacle within the shell sized and shaped to receive at least one article of medical equipment; a second receptacle within the shell sized and shaped to receive a two-way audio-visual system; at least one cover adapted to allow access to the at least one article of medical equipment received within the first receptacle when in an open configuration and to enclose and protect the at least one article of medical equipment received within the first receptacle when in a closed configuration; electrical control circuitry located within the shell and configured for communication with the at least one article of medical equipment and the two-way audio-visual system; communication circuitry for providing communication between the electrical control circuitry and a remote location; and machine-readable indicia accessible from outside the case when the cover is in a closed configuration, the machine-readable indicia encoding information for return of the case from a usage location to a return location; at least one article of medical equipment receivable in the first receptacle; and a two-way audio-visual system receivable in the second receptacle. In addition to the foregoing, other system aspects are described in the claims, drawings, and text forming a part of the disclosure set forth herein.

In an aspect, a method of controlling a medical support system includes receiving at least one status signal indicative of an authorization status with a receiving means in a medical equipment case; generating an electrical lock control signal with electrical control circuitry in the medical equipment case responsive to the at least one status signal; unlocking an electrically controllable lock mechanism responsive to the electrical lock control signal to allow access to at least one article of medical equipment within the medical equipment case responsive to the electrical lock control signal; receiving a signal from the at least one article of medical equipment with the electrical control circuitry; and wirelessly communicating information between the electrical control circuitry and a remote location via communication circuitry in the medical equipment case, wherein the information includes audio-visual information from a two-way audio-visual system in the medical equipment case. In addition to the foregoing, other method aspects are described in the claims, drawings, and text forming a part of the disclosure set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 7 is a flow diagram of a method of controlling a medical support system.

FIG. 8 is a flow diagram of a method of controlling a medical support system.

FIG. 9 is a flow diagram of a method of controlling a medical support system.

FIG. 10 is a flow diagram of a method of controlling a medical support system.

FIG. 11 is a flow diagram of a method of controlling a medical support system.

FIG. 12 is a flow diagram of a method of controlling a medical support system.

FIG. 13 is a flow diagram of a method of controlling a medical support system.

DETAILED DESCRIPTION

Figure 1:
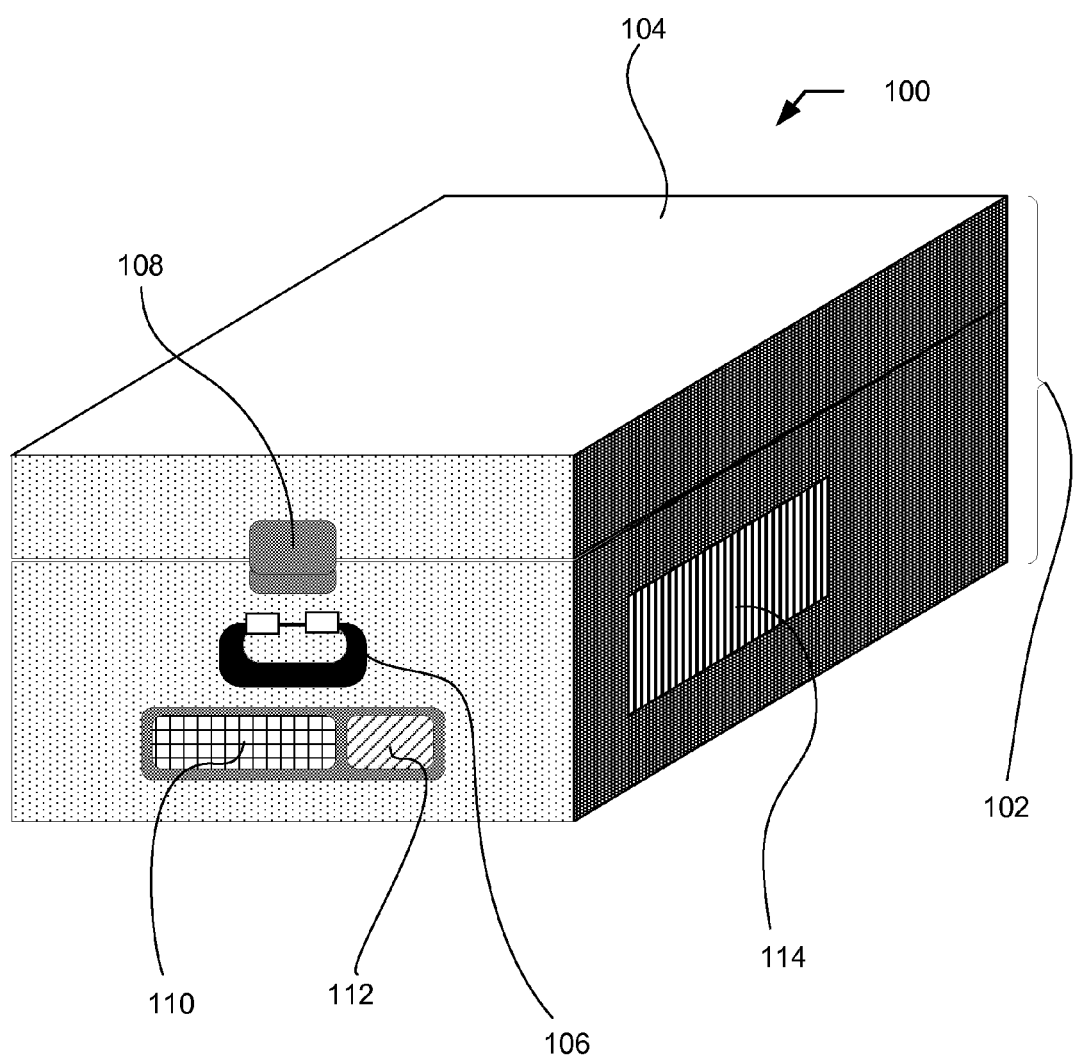
FIG. 1 is an illustration of a medical equipment case.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts a medical equipment case 100 for transporting at least one article of medical equipment. In an aspect, medical equipment case 100 is used by a user (e.g. a medical patient) who requires medical monitoring, but is sufficiently healthy to stay at home. For example, if a patient has been discharged from the hospital but requires further medical monitoring until completely recovered, the patient is discharged from the hospital with medical equipment in medical equipment case 100. In particular, in some aspects the medical equipment case is designed for use in connection with systems in which information is communicated between the medical equipment case and/or equipment stored therein and a central location such as a hospital, for example. In an aspect, medical equipment case 100 includes a number of security features designed to protect the contents of medical equipment case 100, including protecting the medical equipment contained therein as well as protecting the privacy/security of patient information or data which may be stored therein.

As shown in FIG. 1, medical equipment case 100 includes a shell 102, with at least one cover 104 (depicted in a closed configuration in FIG. 1). In an aspect, shell 102 is sized and configured for transport by a human. For example, shell 102 can take the form of a suitcase-style luggage container. In the example of FIG. 1, medical equipment case 100 includes a handle 106. In various aspects, medical equipment case 100 can include one or more fixed handles, extendable handles, wheels, straps, etc. to facilitate transport. Medical equipment case 100 includes at least one electrically controllable lock mechanism 108. In an aspect, medical equipment case 100 also includes user input device 110, a notification system 112 for providing a notification to a user, and machine-readable indicia 114. In an aspect, machine-readable indicia 114 is accessible from outside case 100 when cover 104 is in a closed configuration, and encodes information for return of case 100 from a usage location to a return location. A usage location may be, for example, the patient's home, and the return location may be a hospital or other medical care facility, or medical equipment supply business, from which medical equipment case 100 and the medical equipment contained therein were obtained (e.g., through loan or rental). The user of the medical equipment case may be the patient, or may be a family member or other caregiver, a medical care provider (e.g. visiting nurse), or other party authorized by a medical caregiver and/or the patient to use the medical equipment on behalf of the patient. Medical equipment case 100 can be provided by, communicate with, and/or be controlled by a clinic, hospital, medical care provider, insurance company, or other organization or service provider, for example. Medical equipment case 100 can be provided to a user by loan or rental, for example.

Figure 2:
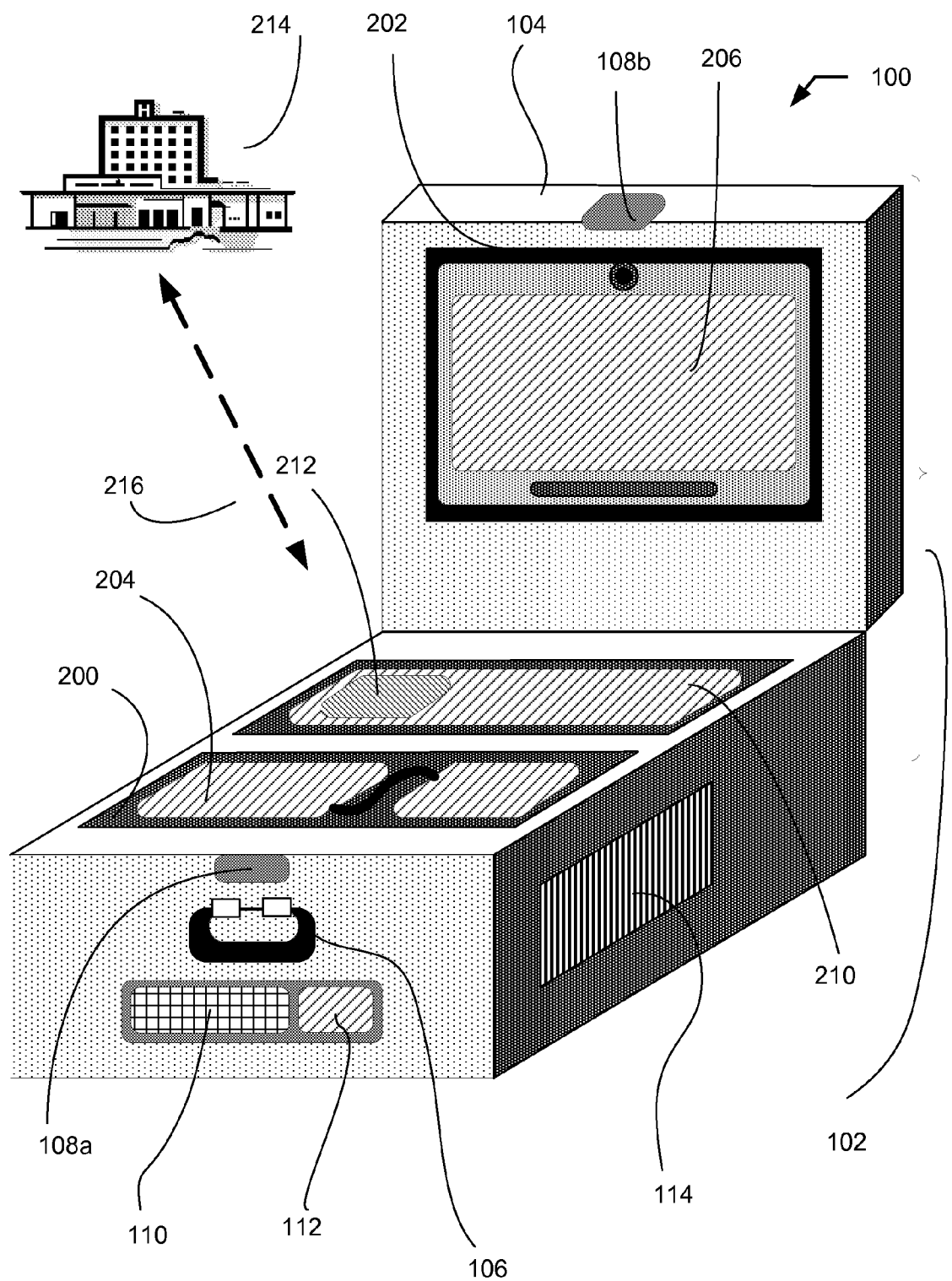
FIG. 2 is an illustration of an opened medical equipment case.

FIG. 2 depicts medical equipment case 100 of FIG. 1 in an open configuration. Components 108a and 108b together form controllable lock mechanism 108 as depicted in FIG. 1. Medical equipment case 100 includes a first receptacle 200 and second receptacle 202 within the shell 102. First receptacle 200 is sized and shaped to receive at least one article of medical equipment 204. Second receptacle 202 is sized and shaped to receive a two-way audio-visual system 206. Cover 104 is adapted to allow access to the at least one article of medical equipment 204 received within first receptacle 200 when in an open configuration (as depicted in FIG. 2) and to enclose and protect the at least one article of medical equipment 204 received within first receptacle 200 when in a closed configuration (as depicted in FIG. 1). Medical equipment case 100 also includes electrical control circuitry 210, which is located within shell 102 and configured for communication with at least one article of medical equipment 204 and two-way audio-visual system 206, and communication circuitry 212, for providing wireless communication between the electrical control circuitry 210 and a remote location 214. For example, in an aspect remote location 214 is a hospital. In other aspects, a remote location can be a clinic, doctor's office, satellite office, or other location that forms a part of a medical care network. Communication between communication circuitry 212 and remote location 214 occurs via one or more wireless signal 216. In an aspect, communication circuitry 212 provides for wireless communication with a remote location 214 via WiFi, cellular network, or other communication network or technology, including but not limited to satellite communication, microwave radio, broadcast radio, microwave radio, free-space optical link, LAN (Local Area Network), MAN (Metropolitan Area Network), WAN (Wide Area Network), infrared WiFi, and Bluetooth.

Figure 3:
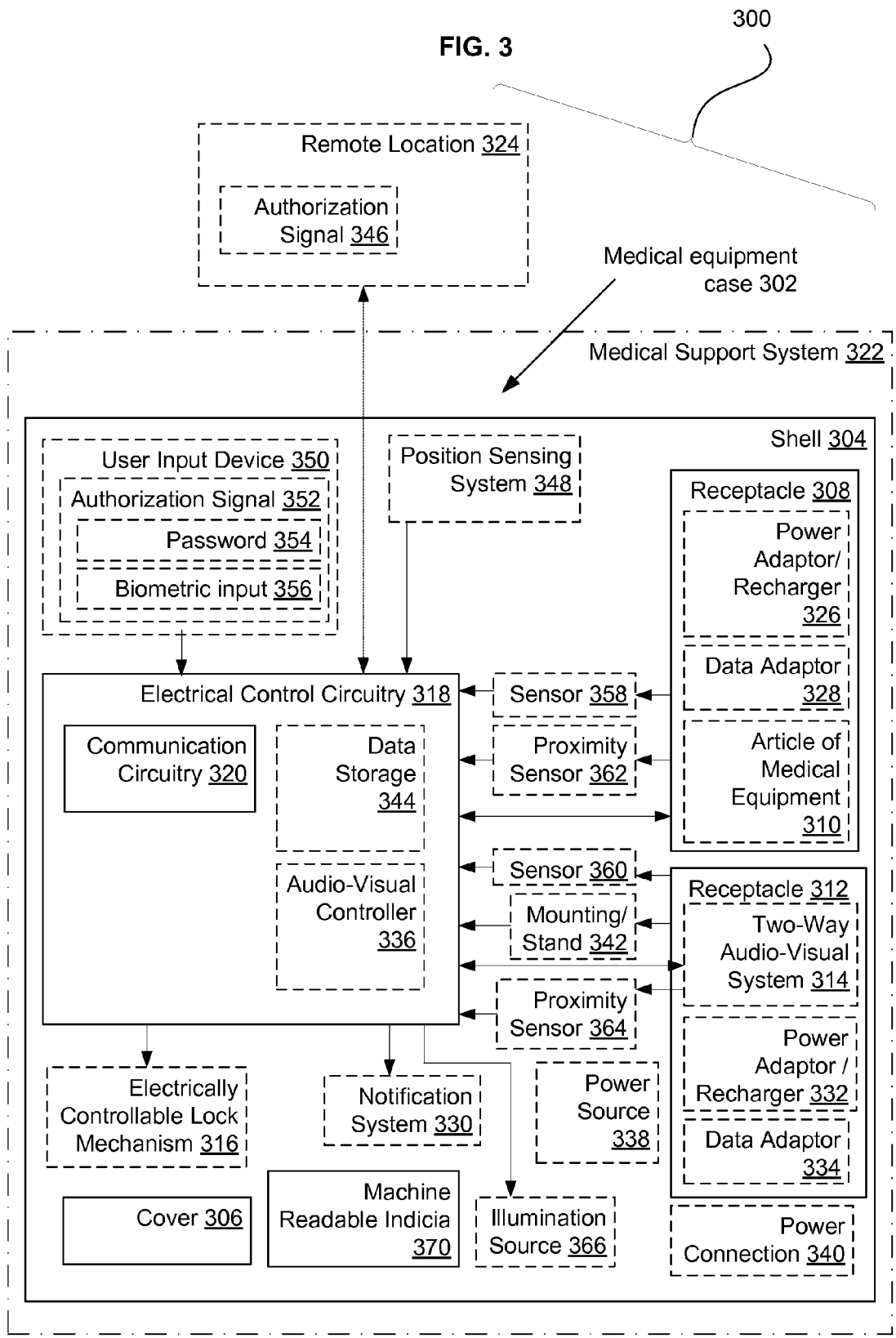
FIG. 3 is a schematic block diagram of a medical support system.

FIG. 3 is a generalized block diagram of a system 300 including a medical equipment case 302. Medical equipment case may include components as described in connection with FIGS. 1 and 2, including, e.g., shell 304, cover 306, at least one receptacle 308 sized and shaped to receive an article of medical equipment 310, and at least one receptacle 312 sized and shaped to receive at least one two-way audio-visual system 314. Shell 304 may be a box-like structure in which cover 306 is a lid, or may take other forms. Cover 306 opens to allow access to at least article of medical equipment 310 received within receptacle 308. In an aspect, as shown e.g. in FIGS. 1 and 2, the cover can allow access not only to one (and potentially more) articles of medical equipment, but to a two-way audio-visual system and potentially other items contained within the medical equipment case, as well. Cover 306 can be movably attached to shell 304, and may pivot, slide, or be lifted away, for example. In an aspect, electrically controllable lock mechanism 316 is configured to lock cover 306 in a closed configuration. In an aspect, medical equipment case 302 includes electrical control circuitry 318 and communication circuitry 320.

In an aspect, a medical equipment case 302 together with at least one article of medical equipment 310 and a two-way audio-visual system 314 form a medical support system 322 (enclosed by alternating dash & dot line in FIG. 3). Such a medical support system can be sent home with a patient who has been discharged from the hospital but would benefit from further medical monitoring.

Medical equipment case 302 can contain one or multiple articles of medical equipment 310. Articles of medical equipment include, but are not limited to, devices for sensing, measuring, collecting samples, and/or delivering treatments, for example. A single medical device may perform one or several such functions. In an aspect, an article of medical equipment includes, for example, a blood pressure cuff or other blood pressure sensor, stethoscope, bioelectromagnetic monitoring device (including a device for sensing EKG, EEG, EMG, EOG, and magnetic and/or electromagnetic correlates thereof, by contact or non-contact methods), bioelectromagnetic stimulation device (including a device for electrical, magnetic and/or electromagnetic stimulation of nerve, muscle and other excitable tissues, defibrillator, TENS unit, etc.), endoscopic device (e.g., a capsule endoscope), cardiac monitoring device (e.g., heart monitor, heart rate monitor, EKG, Holter monitor, etc.), pulse oximeter, touch probe, thermometer, chemical sensor, biosensor, ultrasound probe, blood monitor, bed-mat sensor, electrically controlled medication dispenser, electrically controlled injection device, or electrically controlled infusion device. In various aspects, a chemical sensor can sense chemical(s) in fluid (gas or liquid) or solid/semi-solid samples, for example body fluid, blood, urine, feces, mucous, saliva, sweat, tears, or inspired/expired gas. Sensed chemicals may include, but are not limited to, hydrogen ions (pH), glucose, oxygen or carbon dioxide, hormones, proteins, etc. Biosensors may be used to sense biomolecules, cells, cellular components, and other biological materials or structures, for example, using chemical, immunochemical, and other technologies. Sensed parameters include but are not limited to temperature, pressure, force, electrical or magnetic field, electrical parameters (e.g. current, potential, resistance, resistivity, conductivity, or capacitance), or optical parameters (e.g., absorption, reflection, refraction, or fluorescence). In an aspect, an article of medical equipment includes an imaging device, for example an ultrasonic, acoustic, electromagnetic, optical, visual, x-ray, or other imaging device. In an aspect, devices for delivering treatments include, but are not limited to drug delivery devices, e.g. a pre-stocked pill container, auto needle-based injector, or infusion system. Usage of such devices can be controlled remotely or locally. In an aspect, a drug delivery device is selectively unlocked based on a time schedule or control signal from remote location 324. Usage of a drug delivery device by a user can be confirmed and reported to remote location 324.

Receptacle 308 of medical equipment case 302 can include power adapter/recharger 326 for supplying power to article of medical equipment 310 during use and/or recharging a battery in article of medical equipment 310 between uses, and data adaptor 328 for transfer of data/instructions between article of medical equipment 310 and electrical control circuitry 318 in medical equipment case 302.

Medical support system 322 can display prompts to user via notification system 330 or via two-way audio-visual system 314, to inform user that it is time to make a measurement. Notification system 330 may include one or more audio, visual, tactile, or other types of display device capable of communicating information to a user of the system. Notification system 330 may include components that are detectible when medical equipment case 302 is closed, when it is open, or both. Notification system 330 may include a speaker driven by a sound card to generate an alarm/notification sound or play a pre-recorded or synthesized voice message, or an electrically controlled beeper, buzzer, or bell, for example; one or more lights (e.g. light emitting diodes), segmented or pixelated electronic visual display (e.g., liquid crystal, electrophoretic, electroluminescent, electrochromic, photoluminescent, or electromechnical); a refreshable Braille display, or a haptic interface (based on vibratory motors, electroactive polymers, piezoelectric, electrostatic and subsonic audio wave surface actuation, audio haptics, electrostatic haptics, or electric fields, for example).

Receptacle 312 can include a power adaptor/recharger 332 for supplying power to two-way audio-visual system 314 during use and/or recharging a battery in two-way audio-visual system 314 between uses. Receptacle 312 can include a data adaptor 334 to provide for transfer of data and/or instructions between audio-visual system 314 and electrical control circuitry 318/audio-visual controller 336.

As described previously, medical equipment case includes a shell 304 sized and configured for transport by a human; a first receptacle 308 within shell 304 sized and shaped to receive at least one article of medical equipment 310; a second receptacle 312 within shell 304 sized and shaped to receive a two-way audio-visual system 314; at least one cover 306 adapted to allow access to the at least one article of medical equipment 310 received within the first receptacle 308 when in an open configuration and to enclose and protect the at least one article of medical equipment 310 received within first receptacle 308 when in a closed configuration; electrical control circuitry 318 located within shell 304 and configured for communication with the at least one article of medical equipment 310 and the two-way audio-visual system 314; communication circuitry 320 for providing communication between electrical control circuitry 318 and remote location 324; and machine-readable indicia 370 accessible from outside case 302 when cover 306 is in a closed configuration, the machine-readable indicia encoding information for return of case 302 from a usage location to a return location. Machine-readable indicia 370 may include, for example, a bar code (including linear or two-dimensional bar codes, e.g. a QR code), data tag, (radio frequency identification) RFID, magnetic strip, or various other types of optically, electrically or magnetically detectable code or text. Machine-readable indicia may provide information regarding a return address to which the medical equipment case is to be shipped when the user is done with using it; the address at which the medical equipment case contents are to be used; the contents of the medical equipment case; an identity of one or more owner or user of the medical equipment case, or an identification code associated therewith; pre-paid pickup and delivery arrangements for a shipping service (e.g. UPS or FedEx); etc. Machine-readable indicia may be printed, embossed, or otherwise formed directly on the medical equipment case or applied as an adhesive label or attached to the case in some other manner, for example.

In an aspect, medical equipment case 302 includes power source 338 mounted within shell 304 and configured to supply power to at least one of article of medical equipment 310, two-way audio-visual system 314, electrical control circuitry 318, and communication circuitry 320. Power source 338 may be a battery, solar cell, fuel cell, or energy harvesting device, for example. Alternatively, or in addition, medical equipment case 302 can be provided with a power connection 340 for plugging the medical equipment case 302 into a wall outlet or other power source to supply power to some or all components within the case.

Two-way audio-visual system 314 may be mounted in the receptacle 312, either permanently or temporary. In some cases the two-way audio-visual system 314 is mounted in such a manner that it can be removed prior to use. Two-way audio-visual system 314 may include, for example, one or more camera, video display, microphone, or speaker. Two-way audio-visual system 314 may take the form of an off-the-shelf commercially available device that provides two-way audio-visual capability (e.g., a smart phone or tablet computer), or may be assembled from system components as known to those skilled in the art. In an aspect, two-way audio-visual system 314 is a hand-held device. Two-way audio-visual system 314 may include or be used in combination with an illumination source 366, which may be a component of two-way audio-visual system 314, a component of article of medical equipment 310, a component of medical equipment case 302, or a separate illumination source. In an aspect, illumination source 366 is controllable by electrical control circuitry 318. In an aspect, illumination source 366 is a component of medical support system 322.

In an aspect, two-way audio-visual system 314 is configured to be removed from receptacle 312 and placed on a mounting or stand 342 connected to medical equipment case 302, on the interior or exterior of the medical equipment case 302. In an aspect, mounting or stand 342 is pre-attached to one or both of two-way audio-visual system 314 and medical equipment case 302. A mounting or stand 342 connected to medical equipment case 302 can be extendable and/or include mechanical linkages, hinges, ball joints, etc. that can be adjusted to permit the position of the two-way audio-visual system to be controlled manually by the user or in automated fashion by a remote operator or by a local or remote control system. Control of the position of two-way audio-visual system 314 can be controlled audio-visual controller 336. Audio-visual controller 336 may also control other aspects of operation of two-way audio-visual system 314, including pan, tilt, zoom, recording of audio-visual information, presentation of audio-visual information, etc. In an aspect, two-way audio-visual system 314 is configured to be placed on a mounting or stand that is separate from medical equipment case, or to be placed on any available surface (e.g. a table, a lap of a user, etc.).

In an aspect, two-way audio-visual system 314 is fixedly mounted in the second receptacle, during manufacture or system configuration, so that it is typically removable only when the system is repaired or serviced, or not at all. Mounting of the two-way audio-visual system may be done with a pressure or friction fit, clamps, latches, straps, elastic, screws, rivets, etc., as is known in the art. In an aspect, two-way audio-visual system is movably mounted in the second receptacle, and wherein the two-way audio-visual system is movable between a transport position and a use position, as will be described below in connection with FIGS. 5 and 6.

In an aspect, electrical control circuitry 318 is mounted within shell 304. For example, electrical control circuitry may be packaged as a unit that is mounted in the shell but is removable from the shell (e.g., as part of a computing device mounted in a receptacle in the shell), or it may be installed within the shell such that it is not readily accessible by the user, though it may be accessible for repair, maintenance, or reconfiguration. In an embodiment, electrical control circuitry 318 is connected to or incorporated with two-way audio-visual system 314 or with an article of medical equipment 310.

In an aspect, electrical control circuitry 318 is configured for wireless communication with at least one of the article of medical equipment 310 and the audio-visual system 314, e.g. via communication circuitry 320 in FIG. 3. Communication between electrical control circuitry 318 and remote location 324, via communication circuitry 320, can be via a wireless communication link (e.g. 4G, WiFi, and various communication technologies described elsewhere herein, e.g. in connection with communication circuitry 212). Electrical control circuitry 318 and/or communication circuitry 320 can be preconfigured for communication with remote location 324 such that when the system is turned on by the user it automatically establishes a connection with the remote location, without instruction by the user. Communication between electrical control circuitry 318 and article of medical equipment 310 and two-way audio-visual system 314 can be via wired connection, or via a wireless connection, e.g. radiofrequency or other electromagnetic signal, infrared or other optical signal, using communication technologies such as BlueTooth, ZigBee, local area network (LAN), wireless local area network (WLAN), Body Area Network (BAN), cellular network, or WiFi. In an aspect electrical control circuitry 318 can be configured for either wired or wireless communication in a switchable manner (e.g. through the use of software and/or switchable hardware). In an aspect, electrical control circuitry 318 can be configured for only wired or only wireless communication.

In use, medical equipment case 302 controls access to its contents (e.g., article of medical equipment 310 and/or two-way audio-visual system 314) such that they are not readily accessible to unauthorized parties. For example, controlling access may prevent loss or theft of valuable medical equipment, unauthorized access to patient medical data, or improper use of equipment. Controlling access may also facilitate communication of data and instructions between the authorized user of the medical equipment and personnel at a remote location. Medical equipment case 302 may be openable only by a specific, authorized person (or by a person in possession of authorization information such as a password). Thus, if the medical equipment case 302 and its contents were stolen, the thief would not be able to open the case to access the equipment, or, if the case were opened, would not be able to use the equipment or access confidential information stored in the equipment or at remote location 324 accessible via the medical equipment.

In an aspect, medical equipment case 302 may be openable only in a specific location, as determined by a global positioning system (GPS) or other localization system. By comparing the present location of the medical equipment case 302 with a location stored in a memory on the equipment case (e.g. data storage 344 in electrical circuitry 318) or received by the medical equipment case 302 from a remote location 324, it is possible to control access to the contents of medical equipment case 302 to permit the case to be opened only when it is at the home of the user, for example.

In an aspect, medical equipment case 302 includes at least one electrically controllable lock mechanism 316 configured to lock the cover in the closed configuration. In an aspect electrical control circuitry 318 is configured to control electrically controllable lock mechanism 316 responsive to receipt of an authorization signal 346 from the remote location 324 by the communication circuitry 320. Alternatively, or in addition, medical equipment case 302 may include a key lock or a combination lock.

In an aspect, medical equipment case includes a position sensing system 348 in communication with the electrical control circuitry 318. In an aspect, electrical control circuitry 318 is configured to control the at least one electrically controllable lock mechanism 316 responsive to receipt of a signal from the position sensing system 348 indicative of the medical equipment case being in an authorized location. Position sensing system 348 may be a global positioning system (GPS) or other localization system for example.

In an aspect, medical equipment case 302 includes user input device 350 mounted on an exterior portion of shell 304. In an aspect, electrical control circuitry 318 is configured to control electrically controllable lock mechanism 316 responsive to receipt of an authorization signal 352 from a user via the user input device 350. For example, user input device 350 may be adapted to receive a password 354 from the user (for example, user input device 350 may be a keyboard, keypad, other touch sensitive or touch operated device, or a voice interface adapted for entry of an alphanumeric sequence representing a password, which may include, but is not limited to, an identity or access code). In an aspect, user input device 350 is a digital data reader, which may be, for example, a bar code reader, magnetic strip reader, data tag reader, RFID reader, near field communication (NFC) device or the like, adapted to read a stored password, identity or access code from a linear or two-dimensional bar code, magnetic strip, data tag, RFID, NFC device or chip or the like. In another aspect, user input device 350 may be adapted to receive a biometric input 356 indicative of user identification from the user (for example, a voice signal for voice pattern recognition, image or other data signal for fingerprint recognition, retinal vascularization recognition, facial recognition, or other types of biometric identification signals).

In an aspect, medical equipment case 302 includes at least one sensor 358 for sensing whether the at least one article of medical equipment 310 is present in the first receptacle 308. Medical equipment case 302 includes at least one notification system 330 to provide a notification to a user responsive to sensing that the at least one article of medical equipment 310 is not present in the first receptacle. Similarly, in an aspect medical equipment case 302 also include at least one sensor 360 for sensing whether the two-way audio-visual system 314 is present in the second receptacle 312. In connection therewith, medical equipment case 302 can include at least one notification system 330 that is configured to provide a notification to a user responsive to sensing that the two-way audio-visual system 314 is not present in second receptacle 312. In an aspect, medical equipment case 302 includes a proximity sensor 362 for determining proximity of the at least one article of medical equipment 310 to medical equipment case 302. Proximity sensor 362 may be a wireless proximity sensor, for example. A proximity sensor may be, for example, an infrared sensor, an optical sensor, an electromagnetic sensor, an acoustic sensor, or any other type of sensor suitable for detecting the proximity of the article of medical equipment to the medical equipment case 302. For example, proximity can be determined based on the strength of a signal transmitted from the medical equipment case 302 to the article of medical equipment 310, or vice versa. In another aspect, the proximity of the article of medical equipment to the medical equipment case can be determined based on the strength of a signal transmitted from the medical equipment case, reflected from the article of medical equipment, and detected by proximity sensor 362. In an aspect, medical equipment case 302 includes at least one notification system 330 configured to provide a notification to a user responsive to sensing that the at least one article of medical equipment 310 is not in proximity to the medical equipment case 302. Similarly, in an aspect, medical equipment case 302 includes proximity sensor 364 for determining proximity of two-way audio-visual system 314 to medical equipment case 302. Proximity sensor 364 may be a wireless proximity sensor, or other type of proximity sensor as discussed herein above with regard to proximity sensor 362. In an aspect, medical equipment case 302 includes at least one notification system 330 configured to provide a notification to a user responsive to sensing that the two-way audio-visual system 314 is not in proximity to medical equipment case 302.

By sensing whether the medical device and/or two-way audio-visual are present in the medical equipment case, or in proximity to the medical equipment case, the medical device and/or audio-visual equipment case can be effectively "electronically leashed" to ensure that they are not separated or lost from the medical equipment case. The notification system may provide an audible notification (e.g., generate a beep or squeal, or play a recorded or synthesized voice message) or visible notification (e.g. a flashing light, a text display, etc.) or other detectable notification signal to notify the user that the medical device or two-way audio-visual system is not contained in or in proximity to the medical equipment case. A voice or text message may instruct the user to replace the medical device or two-way audio-visual system in the medical equipment case. The case may be controlled such that it cannot be locked and/or returned until the medical equipment and/or two-way audio-visual system has been returned to the medical equipment case.

Figure 4:
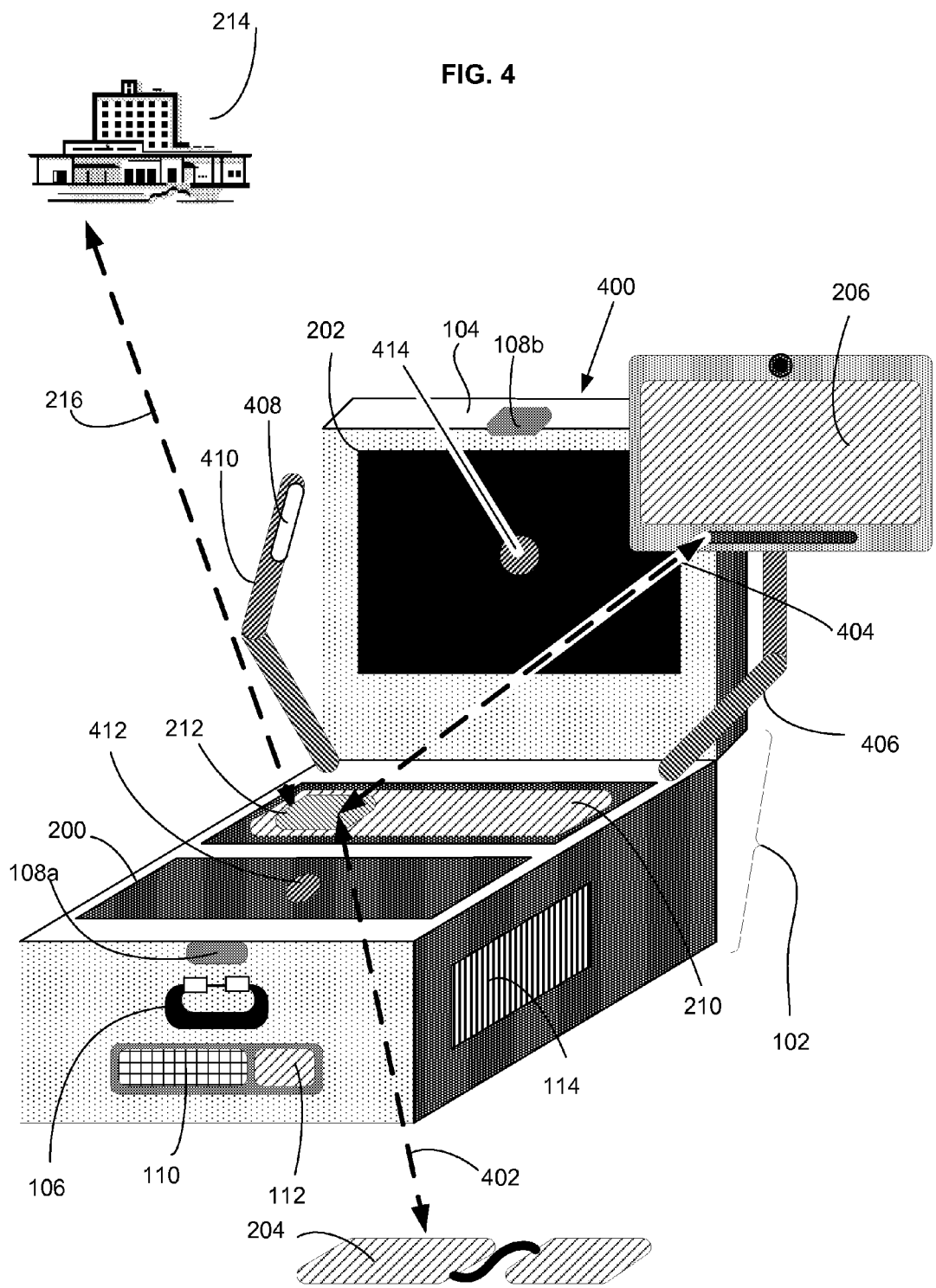
FIG. 4 is an illustration of the medical equipment case of FIG. 2 with medical equipment and two-way audio-visual system removed.

FIG. 4 depicts a system generally as depicted in FIGS. 1 and 2, with the article of medical equipment 204 and two-way audio-visual system 206 removed from medical equipment case 400 for use. During use, data, instructions, and other information are transmitted between article of medical equipment 204 and electrical control circuitry 210 via wireless link 402, and between two-way audio-visual system 206 and electrical control circuitry 210 via wireless link 404. As discussed previously in connection with FIGS. 1 and 2, medical equipment case 400 includes shell 102, cover 104, handle 106, electrically controllable lock mechanism including components 108a and 108b, user input device 110, notification system 112, and machine-readable indicia 114. Two-way audio-visual system 206 is configured to be removed from receptacle 202 and placed on a mounting or stand 406 connected to medical equipment case 400 (here shown in the interior of the medical equipment case 402; alternatively, mounting or stand 406 could be located on the exterior of the medical equipment case). Mounting or stand 406 connected to medical equipment case 400 is depicted as including mechanical linkages joined by hinges and/or ball joints to allow for the position of the two-way audio-visual system to be adjusted. Medical equipment case 400 also includes illumination source 408 on mounting or stand 410, which provides for adjustable positioning and aiming of illumination source 408. In an aspect, mounting or stand 406 and mounting or stand 410 can be folded into medical equipment case 400 when not in use.

As shown in FIG. 4, receptacle 200 includes sensor 412 for detecting whether article of medical equipment 204 is present in receptacle 200. Medical equipment case 400 includes notification system 112 (for example, a light configured to flash, and or a small speaker configured to beep under control of electrical control circuitry 210) to provide a notification to a user responsive to sensing that the at least one article of medical equipment 204 is not present in the first receptacle 200. In various aspects, sensor 400 is an electrical, optical, magnetic, electromagnetic, or electro-mechanical sensor, for example. Medical equipment case 400 also includes at least one sensor 414 for sensing whether the two-way audio-visual system 206 is present in the second receptacle 202. In connection therewith, medical equipment case 100 can include at least one notification system (e.g. notification system 112) that is configured to provide a notification to a user responsive to sensing that the two-way audio-visual system 206 is not present in second receptacle 202. A common notification system can be used to provide notification to a user regarding presence of medical equipment 204 and two-way audio-visual system 206, as depicted in FIG. 4, or, separate notification systems can be used (e.g., separate LEDs that are illuminated to provide notification regarding the two-way audio-visual system and each of one or more articles of medical equipment, respectively).

Figure 5:
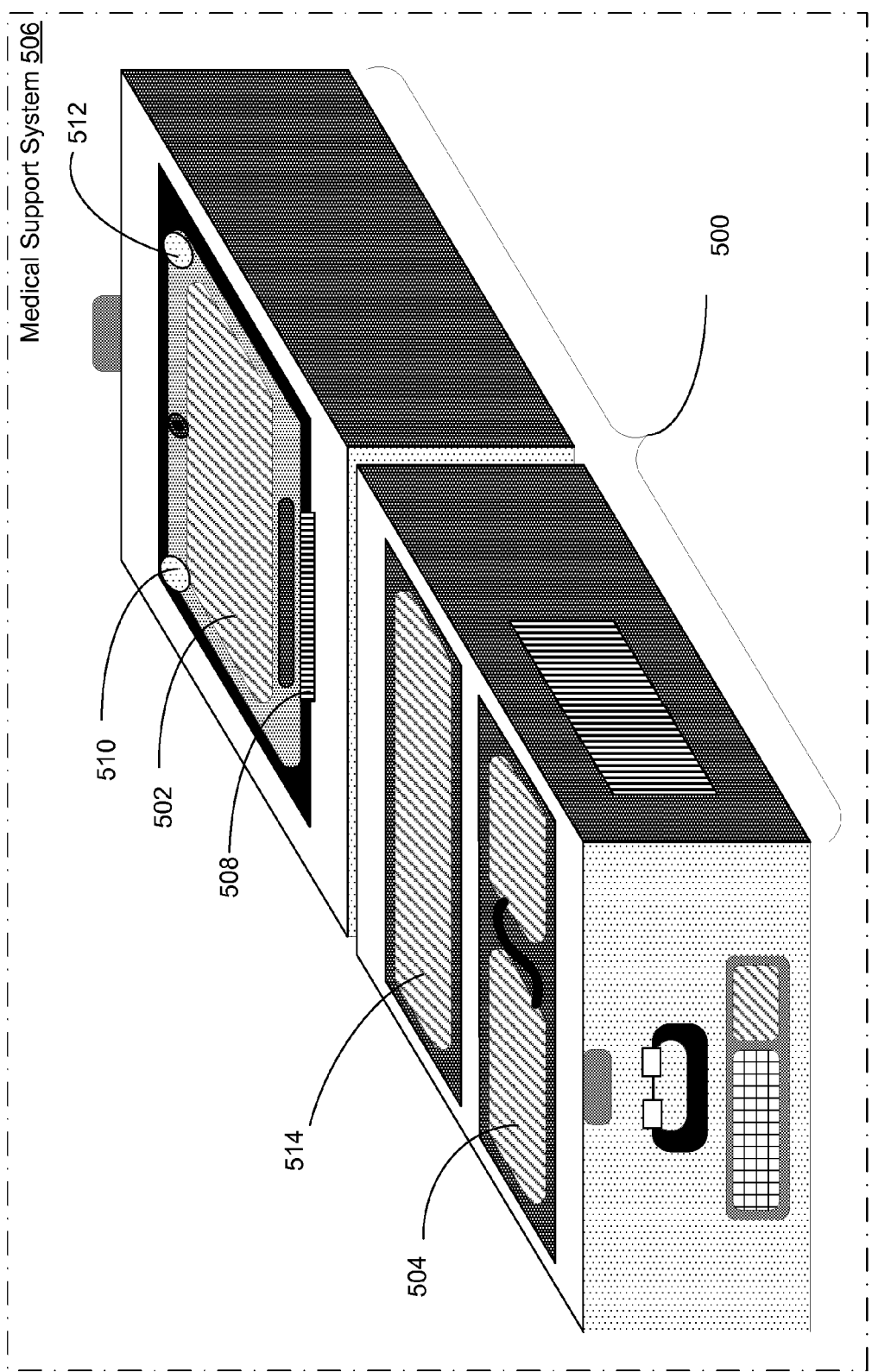
FIG. 5 is an illustration of medical support system including a medical equipment case and a two-way audio-visual system, where the two-way audio-visual system is in a transport position.
Figure 6:
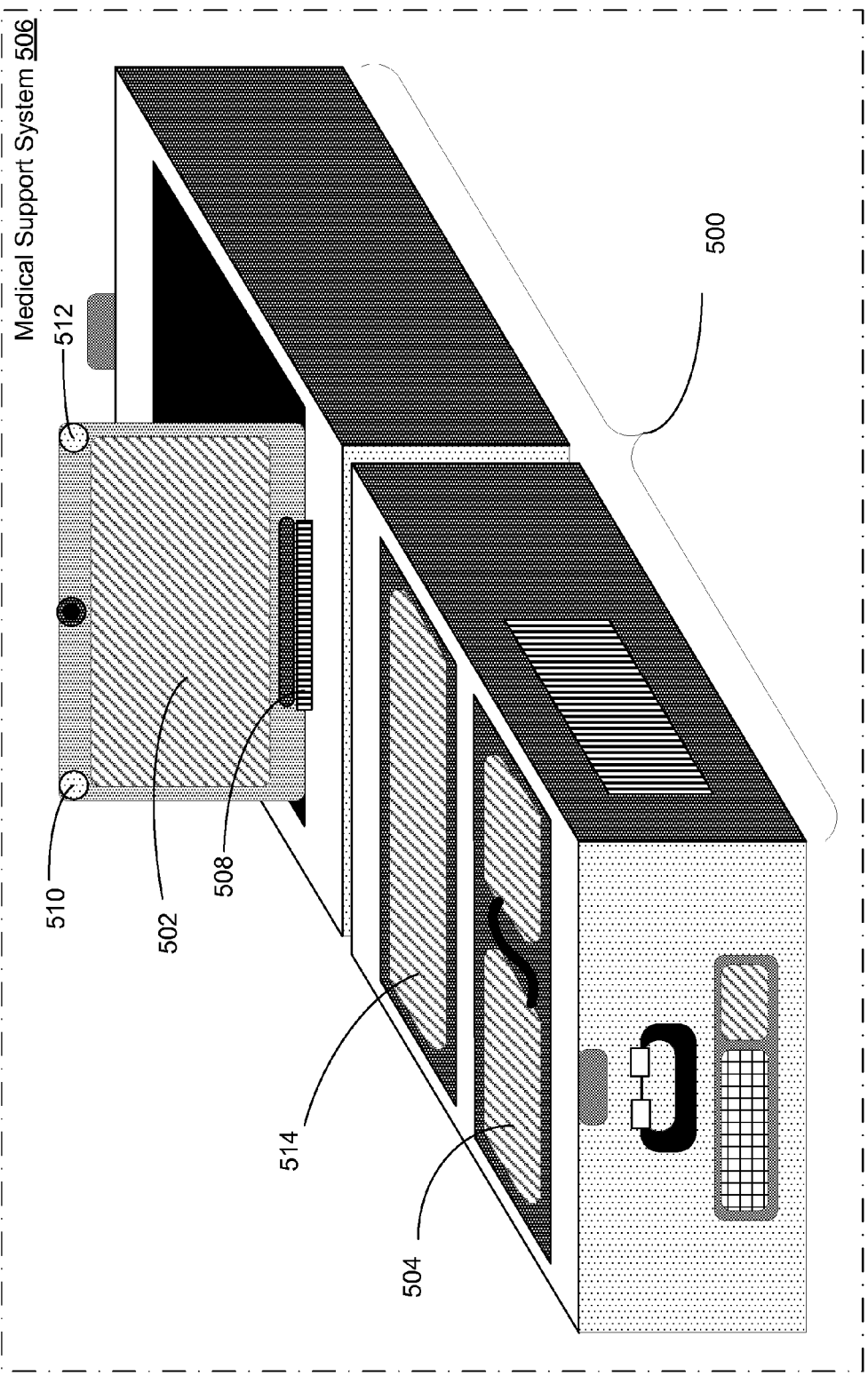
FIG. 6 is an illustration of medical support system of FIG. 5, with the two-way audio-visual system in a use position.

FIGS. 5 and 6 depict a medical equipment case 500, which together with two-way audio-visual system 502 and article of medical equipment 504 comprise medical support system 506. Two-way audio-visual system 502 is movably mounted in medical equipment case 500, by means of hinge 508. FIG. 5 shows two-way audio-visual system 502 folded down into a transport position such that case 500 can be closed for transport, while FIG. 6 shows two-way audio-visual system 502 folded up into a use position. In an aspect, a movable mounting (e.g. hinge 508 in FIGS. 5 and 6, or mounting or stand 406 in FIG. 4) permits the two-way audio-visual system to be positioned to provide a clear line of sight, effective viewing, and comfortable use by the user and a party in a remote location (e.g. a doctor or other medical care provider) for communicating, exchanging information, or otherwise interacting or receiving information via the two-way audio-visual system. A movable mounting may provide for the two-way audio-visual system to be moved by rotation and/or translation in one or more dimensions. A movable mounting may include one or more hinge, sliding mount, ball joint, linkage, and so forth, without limitation.

In an aspect, medical support system 506, which includes medical equipment case 500, one or more article of medical equipment 504, and two-way audio-visual system 502, includes illumination sources 510 and 512. In an aspect, illumination sources 510 and 512 are controllable by electrical control circuitry 514. In the example of FIGS. 5 and 6, illumination sources 510 and 512 are components of two-way audio-visual system 502. In other aspects, only a single illumination source or a larger number of illumination sources may be used.

In a general sense, those skilled in the art will recognize that the various embodiments described herein can be implemented, individually and/or collectively, by various types of electrical circuitry having a wide range of electrical components such as hardware, software, firmware, and/or virtually any combination thereof. Electrical circuitry (including electrical control circuitry 318 depicted in FIG. 3, for example) includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc), and/or any non-electrical analog thereto, such as optical or other analogs (e.g., graphene based circuitry). In a general sense, those skilled in the art will recognize that the various aspects described herein which can be implemented, individually and/or collectively, by a wide range of hardware, software, firmware, and/or any combination thereof can be viewed as being composed of various types of "electrical circuitry."

Those skilled in the art will recognize that at least a portion of the devices and/or processes described herein can be integrated into a data processing system. Those having skill in the art will recognize that a data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Methods pertaining to the operation of systems as depicted in FIGS. 1 through 6 are described in connection with FIGS. 7 through 13.

FIG. 7 depicts a method of controlling a medical support system. Method 700 includes receiving at least one status signal indicative of an authorization status with a receiving means in a medical equipment case, at 702; generating an electrical lock control signal with electrical control circuitry in the medical equipment case responsive to the at least one status signal, at 704; unlocking an electrically controllable lock mechanism responsive to the electrical lock control signal to allow access to at least one article of medical equipment within the medical equipment case responsive to the electrical lock control signal, at 706; receiving a signal from the at least one article of medical equipment with the electrical control circuitry, at 708; and wirelessly communicating information between the electrical control circuitry and a remote location via communication circuitry in the medical equipment case, wherein the information includes audio-visual information from a two-way audio-visual system in the medical equipment case, at 710.

FIGS. 8-13 depict variations and expansions of method 700 as shown in FIG. 7. In the methods depicted in FIGS. 8-13, steps 702-710 are as described generally in connection with FIG. 7. Method steps outlined with dashed lines represent steps that are included in some, but not all method aspects, and combinations of steps other than those specifically depicted in the figures are possible as would be known by those having ordinary skill in the relevant art.

FIG. 8 depicts a method 800, which is an expansion of method 700 shown in FIG. 7. In an aspect of method 800, the information includes medical data acquired with the at least one article of medical equipment, as indicated at 802. In an aspect, the information includes at least one instruction for controlling the at least one article of medical equipment, as indicated at 804. In an aspect, at least a portion of the information is indicative of an identity of a user of the medical support system, as indicated at 806. In an aspect, at least a portion of the information is indicative of an operational status of the medical support system, as indicated at 808. For example, the at least a portion of the information may be indicative of an unactivated operational status of the medical support system, as indicated at 810, an activated operational status of the medical support system, as indicated at 812, a completion-of-use operational status of the medical support system, as indicated at 814, or a malfunctioning operational status of the medical support system, as indicated at 816.

FIG. 9 depicts a method 900, including expansions of step 702 relating to the status signal indicative of an authorization status with a receiving means in the medical equipment case. In an aspect, the at least one status signal is a signal from a position sensing system, and generating the electrical lock control signal responsive to the at least one status signal includes generating the electrical lock control signal to cause unlocking of the electrically controllable lock mechanism responsive to receiving a signal from the position sensing system indicative of the medical equipment case being in an authorized location, as indicated at 902. For example, an authorized location may be the home of the patient, another location frequented by the patient (e.g., the home of a friend or relative, a medical clinic, etc.). One or more authorized locations may be specified before the equipment case is taken from the hospital (or other loan or rental site) based on input from the patient or instructions from the patient's medical care provider, for example. In an aspect, the at least one status signal is an authorization signal from a remote location, and generating the electrical lock control signal responsive to the at least one status signal includes generating the electrical lock control signal to cause unlocking of the electrically controllable lock mechanism responsive to receiving an authorization signal from a remote location, as indicated at 904. In an aspect, the at least one status signal is a user-generated signal from a user input device, and generating the electrical lock control signal responsive to the at least one status signal includes generating the electrical lock control signal to cause unlocking of the electrically controllable lock mechanism responsive to receiving a user-generated signal indicative of the medical equipment case being used by an authorized user, as indicated at 906. In further aspects, the at least one status signal may be a biometric input indicative of user identity, indicated at 908, or a password, as indicated at 910.

FIG. 10 depicts a method 1000, which includes steps 702, 704, 706, 708, and 710 as described in connection with FIG. 7. In addition, method 1000 includes detecting whether the at least one article of medical equipment is located within the medical equipment case, as indicated at 1002. In an aspect, method 1000 also includes activating a notification system in the medical equipment case to provide a notification to a user responsive to sensing that the at least one article of medical equipment is not located within the medical equipment case, as indicated at 1004, generating the electrical lock control signal with the electrical control circuitry in the medical equipment case to cause locking of the electrically controllable lock mechanism responsive to sensing that the at least one article of medical equipment is located within the medical equipment case, as indicated at 1006, or generating the electrical lock control signal with the electrical control circuitry in the medical equipment case to prevent locking of the electrically controllable lock mechanism responsive to sensing that the at least one article of medical equipment is not located within the medical equipment case, as indicated at 1008. Thus, if the medical equipment has been returned to the case, the case will be permitted to lock so that the user can return it to the hospital or other return location, whereas if the user has failed to return the article of medical equipment to the medical equipment case, the user will not be able to lock the case in and return it to the hospital or other return location until the equipment has been return to the case. Thus, the risk of the medical equipment case being returned to with one or more article of medical equipment missing is reduced.

FIG. 11 depicts a method 1100, which includes steps 702, 704, 706, 708, and 710 as described in connection with FIG. 7, and which also includes detecting whether the two-way audio-visual system is located within the medical equipment case, as indicated at 1102. In an aspect, method 1100 also includes activating a notification system in the medical equipment case to provide a notification to a user responsive to sensing that the two-way audio-visual system is not located within the medical equipment case, as indicated at 1104, generating the electrical lock control signal with the electrical control circuitry in the medical equipment case to cause locking of the electrically controllable lock mechanism responsive to sensing that the two-way audio-visual system is located within the medical equipment case, as indicated at 1106, or generating the electrical lock control signal with the electrical control circuitry in the medical equipment case to prevent locking of the electrically controllable lock mechanism responsive to sensing that the two-way audio-visual system is not located within the medical equipment case, as indicated at 1108. Thus, if the two-way audio-visual system has been returned to the case, the case will be permitted to lock so that the user can return it to the hospital or other return location, whereas if the user has failed to return the two-way audio-visual system to the medical equipment case, the user will not be able to lock the case in and return it to the hospital or other return location until the equipment has been return to the case. Thus, the risk of the medical equipment case being returned to without two-way audio-visual system is reduced.

FIG. 12 depicts a method 1200, which includes steps 702, 704, 706, 708, and 710 as described in connection with FIG. 7, and which also includes sensing proximity of the at least one article of medical equipment to the medical equipment case, as indicated at 1202. In an aspect, method 1200 includes activating a notification system in the medical equipment case to provide a notification to a user responsive to sensing that the at least one article of medical equipment is not within a specified proximity to the medical equipment case, as indicated at 1204, generating the electrical lock control signal with the electrical control circuitry in the medical equipment case to cause locking of the electrically controllable lock mechanism responsive to sensing that the at least one article of medical equipment is within a specified proximity to the medical equipment case, as indicated at 1206, or generating the electrical lock control signal with the electrical control circuitry in the medical equipment case to prevent locking of the electrically controllable lock mechanism responsive to sensing that the at least one article of medical equipment is not within a specified proximity to the medical equipment case, as indicated at 1208.

FIG. 13 depicts a method 1300, which includes steps 702, 704, 706, 708, and 710 as described in connection with FIG. 7, and which also includes sensing proximity of the two-way audio-visual system to the medical equipment case, as indicated at 1302. In an aspect, method 1300 also includes activating a notification system in the medical equipment case to provide a notification to a user responsive to sensing that the two-way audio-visual system is not within a specified proximity to the medical equipment case, as indicated at 1304, generating the electrical lock control signal with the electrical control circuitry in the medical equipment case to cause locking of the electrically controllable lock mechanism responsive to sensing that the two-way audio-visual system is within a specified proximity to the medical equipment case, as indicated at 1306, or generating the electrical lock control signal with the electrical control circuitry in the medical equipment case to prevent locking of the electrically controllable lock mechanism responsive to sensing that the two-way audio-visual system is not within a specified proximity to the medical equipment case, as indicated at 1308.

In various embodiments, methods as described herein may be performed according to instructions implementable in hardware, software, and/or firmware. Such instructions may be stored in non-transitory machine-readable data storage media, for example. Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electrical circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled// implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode (s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may also include transmission type medium such as a digital and/or an analog communication medium (e.g., a fiber optic cable, a waveguide, a wired communications link, a wireless communication link (e.g., transmitter, receiver, transmission logic, reception logic, etc) and so forth).

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A medical equipment case comprising:
   a shell sized and configured for transport by a human;
   a first receptacle within the shell sized and shaped to receive at least one article of medical equipment;
   a second receptacle within the shell sized and shaped to receive a two-way audio-visual system;
   at least one cover adapted to allow access to the at least one article of medical equipment received within the first receptacle when in an open configuration and to enclose and protect the at least one article of medical equipment received within the first receptacle when in a closed configuration;
   electrical control circuitry located within the shell and configured for communication with the at least one article of medical equipment and the two-way audio-visual system;
   communication circuitry for providing wireless communication between the electrical control circuitry and a remote location; and
   machine-readable indicia accessible from outside the case when the cover is in a closed configuration, the machine-readable indicia encoding information for return of the case from a usage location to a return location.

2. The medical equipment case of claim 1, further including the two-way audio-visual system mounted in the second receptacle.

3. The medical equipment case of claim 2, wherein the two-way audio-visual system is movably mounted in the second receptacle, and wherein the two-way audio-visual system is movable between a transport position and a use position.

4. The medical equipment case of claim 1, further including at least one electrically controllable lock mechanism configured to lock the cover in the closed configuration.

5. The medical equipment case of claim 4, wherein the electrical control circuitry is configured to control the at least one electrically controllable lock mechanism responsive to receipt of an authorization signal from the remote location by the communication circuitry.

6. The medical equipment case of claim 4, further including a position sensing system in communication with the electrical control circuitry, wherein the electrical control circuitry is configured to control the at least one electrically controllable lock mechanism responsive to receipt of a signal from the position sensing system indicative of the medical equipment case being in an authorized location.

7. The medical equipment case of claim 4, further including a user input device mounted on an exterior portion of the shell, wherein the electrical control circuitry is configured to control the at least one electrically controllable lock mechanism responsive to receipt of an authorization signal from a user via the user input device.

8. The medical equipment case of claim 1, further including at least one of:
a power source mounted within the shell configured to supply power to at least one of the article of medical equipment, the two-way audio-visual system, the electrical control circuitry, and the communication circuitry; and
a position sensing system in communication with the electrical control circuitry.

9. The medical equipment case of claim 1, wherein the electrical control circuitry is mounted within the shell and configured for at least one of wireless communication and wired communication with at least one of the article of medical equipment and the audio-visual system.

10. The medical equipment case of claim 7, wherein the user input device includes at least one of a keyboard, a keypad, a touch sensitive device, a touch operated device, a voice interface, a digital data reader, a bar code reader, a magnetic strip reader, a data tag reader, an RFID reader, and a near field communication device.

11. The medical equipment case of claim 7, wherein the user input device is adapted to do at least one of read a stored identity or access code, receive a password from the user, receive a biometric input indicative of user identification from the user, receive a voice signal, or receive an image.

12. The medical equipment case of claim 1, further including at least one of a sensor for sensing whether the at least one article of medical equipment is present in the first receptacle, and a sensor for sensing whether the two-way audio-visual system is present in the second receptacle.

13. The medical equipment case of claim 12, further including at least one notification system configured to provide a notification to a user responsive to sensing at least one of that the at least one article of medical equipment is not present in the first receptacle and the two-way audio-visual system is not present in the second receptacle.

14. The medical equipment case of claim 1, further including a wireless proximity sensor for determining proximity of at least one of the at least one article of medical equipment and the two-way audio-visual system to the medical equipment case.

15. The medical equipment case of claim 14, further including at least one notification system configured to provide a notification to a user responsive to sensing that at least one of the at least one article of medical equipment and the two-way audio-visual system is not in proximity to the medical equipment case.

16. A medical support system, comprising:
a medical equipment case including:
a shell sized and configured for transport by a human;
a first receptacle within the shell sized and shaped to receive at least one article of medical equipment;
a second receptacle within the shell sized and shaped to receive a two-way audio-visual system;
at least one cover adapted to allow access to the at least one article of medical equipment received within the first receptacle when in an open configuration and to enclose and protect the at least one article of medical equipment received within the first receptacle when in a closed configuration;
electrical control circuitry located within the shell and configured for communication with the at least one article of medical equipment and the two-way audio-visual system;
communication circuitry for providing communication between the electrical control circuitry and a remote location; and
machine-readable indicia accessible from outside the case when the cover is in a closed configuration, the machine-readable indicia encoding information for return of the case from a usage location to a return location;
at least one article of medical equipment receivable in the first receptacle; and
a two-way audio-visual system receivable in the second receptacle.

17. The system of claim 16, further including a power source mounted within the shell configured to supply power to at least one of the article of medical equipment, the two-way audio-visual system, the electrical control circuitry, and the communication circuitry.

18. The system of claim 16, further including an illumination source controllable by the electrical control circuitry.

19. The system of claim 16, wherein the at least one article of medical equipment includes at least one of a blood pressure sensor, a stethoscope, a touch probe, a thermometer, a heart rate sensor, a pulse oximeter, an ultrasound probe, a chemical sensor, an endoscopic device, a cardiac monitoring device, a biosensor, a bioelectromagnetic monitoring device, a bioelectromagnetic stimulation device, an electrically controlled medication dispenser, an electrically controlled injection device, and an electrically controlled infusion device.

20. The system of claim 16, wherein the two-way audio-visual system includes at least one of a camera, a video display, a microphone, and a speaker.

21. A method of controlling a medical support system comprising:
receiving at least one status signal indicative of an authorization status with a receiving means in a medical equipment case, the medical equipment case including a shell, a movable cover, and an electrically controllable lock configured to lock the medical equipment case in a closed configuration;
generating an electrical lock control signal with electrical control circuitry in the medical equipment case responsive to the at least one status signal;
unlocking the electrically controllable lock mechanism responsive to the electrical lock control signal to allow access to at least one article of medical equipment within the medical equipment case responsive to the electrical lock control signal by allowing movement of the cover of the medical equipment case from the closed configuration to an open configuration;

receiving a signal from the at least one article of medical equipment with the electrical control circuitry; and wirelessly communicating information between the electrical control circuitry and a remote location via communication circuitry in the medical equipment case, wherein the information includes audio-visual information from a two-way audio-visual system in the medical equipment case.

22. The method of claim 21, wherein the at least one status signal is a signal from a position sensing system, and wherein generating the electrical lock control signal responsive to the at least one status signal includes generating the electrical lock control signal to cause unlocking of the electrically controllable lock mechanism responsive to receiving a signal from the position sensing system indicative of the medical equipment case being in an authorized location.

23. The method of claim 21, wherein the at least one status signal is an authorization signal from a remote location, and wherein generating the electrical lock control signal responsive to the at least one status signal includes generating the electrical lock control signal to cause unlocking of the electrically controllable lock mechanism responsive to receiving an authorization signal from a remote location.

24. The method of claim 21, wherein the at least one status signal is a user-generated signal from a user input device, and wherein generating the electrical lock control signal responsive to the at least one status signal includes generating the electrical lock control signal to cause unlocking of the electrically controllable lock mechanism responsive to receiving a user-generated signal indicative of the medical equipment case being used by an authorized user.

25. The method of claim 21, wherein the information includes at least one of medical data acquired with the at least one article of medical equipment and at least one instruction for controlling the at least one article of medical equipment.

26. The method of claim 21, wherein at least a portion of the information is indicative of at least one of an identity of a user of the medical support system and an operational status of the medical support system.

27. The method of claim 26, wherein the at least a portion of the information is indicative of an operational status of the medical support system, wherein the operational status of the medical support system is selected from an unactivated operational status, an activated operational status, a completion-of-use operational status, and a malfunctioning operational status.

28. The method of claim 24, wherein the at least one status signal includes at least one of a biometric input indicative of user identity and a password.

29. The method of claim 21, further including detecting whether at least one of the at least one article of medical equipment and the two-way audio-visual system is located within the medical equipment case.

30. The method of claim 29, further including at least one of:

activating a notification system in the medical equipment case to provide a notification to a user responsive to sensing that the at least one of the at least one article of medical equipment and the two-way audio-visual system is not located within the medical equipment case;

generating the electrical lock control signal with the electrical control circuitry in the medical equipment case to cause locking of the electrically controllable lock mechanism responsive to sensing that the at least one of the at least one article of medical equipment and the two-way audio-visual system is not located within the medical equipment case; and generating the electrical lock control signal with the electrical control circuitry in the medical equipment case to prevent locking of the electrically controllable lock mechanism responsive to sensing that the at least one of the at least one article of medical equipment and the two-way audio-visual system is not located within the medical equipment case.

31. The method of claim 21, further including sensing proximity of at least one of the at least one article of medical equipment and the two-way audio-visual system to the medical equipment case.

32. The method of claim 31, further including at least one of:

activating a notification system in the medical equipment case to provide a notification to a user responsive to sensing that the at least one of the at least one article of medical equipment and the two-way audio-visual system is not within a specified proximity to the medical equipment case;

generating the electrical lock control signal with the electrical control circuitry in the medical equipment case to cause locking of the electrically controllable lock mechanism responsive to sensing that the at least one of the at least one article of medical equipment and the two-way audio-visual system is within a specified proximity to the medical equipment case; and generating the electrical lock control signal with the electrical control circuitry in the medical equipment case to prevent locking of the electrically controllable lock mechanism responsive to sensing that the at least one of the at least one article of medical equipment and the two-way audio-visual system is not within a specified proximity to the medical equipment case.

* * * * *